United States Patent
Manhart

(10) Patent No.: US 11,222,411 B2
(45) Date of Patent: Jan. 11, 2022

(54) METHOD FOR AUTOMATICALLY ADAPTING AN IMAGE DATA SET OBTAINED BY AN X-RAY DEVICE

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 393 days.

(21) Appl. No.: 16/445,501

(22) Filed: Jun. 19, 2019

(65) Prior Publication Data
US 2019/0392563 A1    Dec. 26, 2019

(30) Foreign Application Priority Data
Jun. 20, 2018 (EP) .................................. 18178807

(51) Int. Cl.
*G06K 9/00*       (2006.01)
*G06T 5/00*       (2006.01)
(Continued)

(52) U.S. Cl.
CPC ............ *G06T 5/009* (2013.01); *A61B 6/5258* (2013.01); *G06T 5/001* (2013.01); *G06T 5/007* (2013.01);
(Continued)

(58) Field of Classification Search
CPC ........... G06T 5/00; G06T 5/001; G06T 5/002; G06T 5/006; G06T 5/007; G06T 5/008;
(Continued)

(56) References Cited

U.S. PATENT DOCUMENTS

| | | | | |
|---|---|---|---|---|
| 6,463,167 B1 * | 10/2002 | Feldman | ............... | G06T 7/0012 382/128 |
| 6,546,124 B1 * | 4/2003 | Hopple | ................... | G06T 5/008 382/131 |

(Continued)

FOREIGN PATENT DOCUMENTS

| | | |
|---|---|---|
| CN | 103536360 A | 1/2014 |
| JP | 2011000439 A | 1/2011 |
| JP | 2013252449 A | 12/2013 |

OTHER PUBLICATIONS

Chinese Office Action for Chinese Application No. 201910530548.X dated Dec. 4, 2020, with English translation.
(Continued)

*Primary Examiner* — Eric Rush
(74) *Attorney, Agent, or Firm* — Lempia Summerfield Katz LLC

(57) ABSTRACT

A method and system for automatically adapting an image data set obtained by an X-ray device. Binary masks are generated for single images of the image data set. The masks differentiate different components of an imaged target object from each other. A reference image of the image data set is determined therefrom, that contains a largest cohesive region of one of the components. From a mean value determined for the region and a specified target value, an offset is determined in such a way that by applying it to the pixel values used for determining the mean value. The pixel values are adapted in such a way that a mean value of the pixel values adapted by the offset corresponds to the specified target value. The determined offset is then applied to all pixel values of the image data set in order to adapt the image data set.

18 Claims, 3 Drawing Sheets

(51) Int. Cl.
  *G06T 5/20* (2006.01)
  *G06T 5/50* (2006.01)
  *A61B 6/00* (2006.01)
  *G06T 7/00* (2017.01)

(52) U.S. Cl.
  CPC ............... *G06T 5/008* (2013.01); *G06T 5/20* (2013.01); *G06T 5/50* (2013.01); *G06T 7/0012* (2013.01); *G06T 2207/10116* (2013.01); *G06T 2207/20208* (2013.01); *G06T 2207/30004* (2013.01); *G06T 2207/30016* (2013.01)

(58) Field of Classification Search
  CPC ............ G06T 5/009; G06T 5/20; G06T 5/30; G06T 5/50; G06T 7/0012; G06T 7/10; G06T 7/11; G06T 7/136; G06T 7/187; G06T 7/62; G06T 2207/10081; G06T 2207/10116; G06T 2207/20036; G06T 2207/20172; G06T 2207/20208; G06T 2207/30004; G06T 2207/30016; G06T 2207/30061; G06T 2207/30096; G06K 9/2054; G06K 9/34; G06K 9/342; G06K 9/62; G06K 2209/05; G06K 2209/051; G06K 2209/053; G06K 2209/055; A61B 5/004; A61B 5/0042; A61B 6/02; A61B 6/03; A61B 6/032; A61B 6/501; A61B 6/5205; A61B 6/5217; A61B 6/5258; A61B 6/5294; A61B 6/582; A61B 8/5269; A61B 257/026; G16H 30/20; G16H 50/20; G16H 50/30
  USPC ....... 382/103, 128, 131, 132, 154, 168, 169, 382/171–173, 254, 257, 260, 264, 270, 382/272, 274, 275, 282, 283; 250/363.07, 250/363.09, 370.09, 587; 378/4, 5, 8, 16, 378/21, 62, 98.7; 345/419, 424, 426, 345/589, 590, 617, 625, 626; 600/407, 600/425, 442, 458; 128/920, 922
  See application file for complete search history.

(56) References Cited

U.S. PATENT DOCUMENTS

| | | | | |
|---|---|---|---|---|
| 6,584,216 | B1* | 6/2003 | Nyul | G06T 5/009 |
| | | | | 382/131 |
| 9,224,201 | B2* | 12/2015 | Kohler | G06T 7/0012 |
| 9,858,674 | B2* | 1/2018 | Lachner | G06T 7/0012 |
| 2003/0095696 | A1* | 5/2003 | Reeves | G06T 7/0012 |
| | | | | 382/131 |
| 2010/0322488 | A1 | 12/2010 | Virtue et al. | |
| 2011/0286649 | A1 | 11/2011 | Reisman | |
| 2014/0010428 | A1 | 1/2014 | Schmidt | |

OTHER PUBLICATIONS

Japanese Office Action for Japanese Application No. 2019-094472 dispatched Dec. 15, 2020, with English translation.
Kim, Seong-Hoon, et al. "X-ray image classification using random forests with local binary patterns" 2010 International Conference on Machine Learning and Cybernetics. Vol. 6. IEEE, 2010. pp. 3190-3194.-.
Wang, Yukun et al: "Recognition and Processing of Computer Image In Medicine" vol. 15; No. 4; Aug. 31, 1995; pp. 1-4 with Abstract.
Dunlop, Alex, et al. "Comparison of CT number calibration techniques for CBCT-based dose calculation." Strahlentherapie und Onkologie 191.12 (2015): 970-978.
European Search Report for European Patent Application No. 18178807.6-1124 dated Dec. 20, 2018, with English Translation.
Joshi, K. D., T. E. Marchant, and C. J. Moore. "Shading correction algorithm for cone-beam CT in radiotherapy: extensive clinical validation of image quality improvement." Medical Imaging 2017: Physics of Medical Imaging. vol. 10132. International Society for Optics and Photonics, 2017.

* cited by examiner

METHOD FOR AUTOMATICALLY ADAPTING AN IMAGE DATA SET OBTAINED BY AN X-RAY DEVICE

CROSS REFERENCE TO RELATED APPLICATIONS

This application claims the benefit of EP18178807.6, filed on Jun. 20, 2018, which is hereby incorporated by reference in its entirety.

FIELD

Embodiments relate to a method for automatically adapting a medical image data set,

BACKGROUND

Current methods and X-ray devices provide high-quality imaging of individual target objects or patients. However, when imaging a plurality of different patients, different pixel or intensity values nevertheless result in the corresponding X-ray images for the same types of tissue. This may be caused, for example by individual properties of the respectively used X-ray device, such as, for instance a different or inaccurate calibration or different frequencies or spectra of the X-ray radiation used. If, in practice, the X-ray radiation used is not actually monochromatic, then this may lead to beam hardening and/or other non-linear effects, that may ultimately affect obtained image data. Due to these differences between scans of different patients and/or scans of the same patient by different X-ray devices, a reliable and consistent application of standardized processing or evaluation methods to the obtained X-ray images or image data may be rendered difficult.

BRIEF SUMMARY AND DESCRIPTION

The scope of the present invention is defined solely by the appended claims and is not affected to any degree by the statements within the summary. The present embodiments may obviate one or more of the drawbacks or limitations in the related art.

Embodiments improve consistency and usability of X-ray image data.

A method is used for automatically adapting an image data set obtained by an X-ray device, that maps a target object. The image data set is acquired in one method step of the method. The image data set includes a plurality of single images, that map different slices or planes of the target object or correspond thereto. The image data set may be or constitute a volume reconstructed using known methods. Acquisition of the image data set may include imaging the target object by the X-ray device. Acquisition of the image data set may also retrieve the image data set, for example, from a data memory or a corresponding data memory on which the image data set is stored, supplies it to a corresponding data processing facility adapted for carrying out the method and is recognized or read in by the facility. The target object may ultimately be any object or any article, but it may be a patient or a section of a patient, for example a particular organ or a region of tissue. The image data set maps, for example, a specific target tissue or a specific target tissue type, for example brain tissue, of the target object, that is of interest, for example for an examination, assessment or diagnosis of the patient respectively.

In a further act, a respective binary mask, e.g. a respective binary mask image, is generated for each of the single images using at least one specified threshold value. The binary masks differentiate different components of the target object in the single images from each other. A binary mask is an image associated with the respective single image or an amount of data associated with the respective single image, that includes or contains only two different values. The respective binary mask indicates pixel by pixel or pixel accurately for the respective single image whether the respective pixel maps a particular component or tissue type of the target object or not. A value on the Hounsfield scale may be specified as the specified threshold value, and may lie for instance between typical values for bone and for soft tissue. To generate the respective binary mask, a check is then made for each pixel of the respective single image as to whether the pixel's intensity or brightness value lies above or below the specified threshold value on the Hounsfield scale, in other words in Hounsfield units (HU). Depending on the result, one or the other of the two binary values, for example 1 or 0, is defined for a respective corresponding pixel of the binary mask. By way of the binary mask an initially rough distinction may therefore be made between the different components or types of material of the target object.

In a further method act, using all of the binary masks, that one of the single images is determined that contains the largest cohesive region of one of the components, for example, of a specified component. The determined single image is determined or selects as the reference image for the further method. The reference image is therefore one of the single images, in which the pixels associated with the corresponding component or mapping the component form the largest cohesive region or grouping. A cohesive region is a group or quantity of pixels of one of the single images respectively. All pixels of the cohesive region include intensity or Hounsfield values, that lie on the same side of the threshold value used to generate the binary masks. Furthermore, every other pixel of the cohesive region may be reached from every pixel of the cohesive region, in which a jump is made as often as necessary to an immediately adjacent pixel of the cohesive region. Every pixel of the cohesive region is therefore connected to a remainder of the cohesive region by pixels of the cohesive region. A cohesive region is defined for one of the binary masks respectively, where all pixels of a cohesive region include the same of the two binary values of the mask.

In a further method act of the method a mean value of all pixel values of the reference image pertaining to the largest cohesive region is determined. The mean value of all pixel values, that is to say intensity or HU values, of the pixels of the reference image that form the determined largest cohesive region is calculated.

In a further method act of the method an offset is determined or calculated from the determined mean value and a specified target value. The offset is determined such that by applying the offset to the pixel values used for determining the mean value, e.g. the pixels of the determined largest cohesive region. The pixels are adapted in such a way that a mean value of the pixel values of the pixels adapted by the offset corresponds to the specified target value. All pixels or pixel values of the cohesive region may be adapted in the same way by the offset. It may be specified how the offset should be applied to the pixels or pixel values, for example in the form of or according to a specified mathematical equation, linking or function. The target value may be predefined specifically for at least one of the components differentiated or distinguished by the specified threshold value or the binary masks. For example, a particular CT number or a particular HU value, in other words a particular value on the Hounsfield scale, may be specified as the target value. Depending on the kind or type of respective component, the target value may be for example an empirical value or a typical value from previous image data sets of other target objects.

In a further method step of the method the determined offset for adapting the image data set is applied to all pixel values or pixels of the image data set. All pixels or pixel values of all single images of the image data set are adapted in the same way, therefore. The adaptation occurs according to the mathematical function, dependency or equation that is also used as a basis when determining the offset.

The image data set may be automatically adapted or corrected by the method such that consistent imaging or mapping of the target object reliably results. This is made possible by the dynamic and individual determination of the offset for the respective image data set irrespective of with which X-ray device the target object was imaged. A normalization of the intensity or HU values of the image data set is achieved by the method. As a result, image data sets of different target objects may be compared with each other consistently, reliably and meaningfully, for example, when the image data sets map the same components, in other words target tissue or target tissue types. The absolute HU values of the image data set are adapted by the method in such a way therefore that the image data set may automatically then be consistently and correctly processed further by additional algorithms or methods, that are based on HU threshold values or distinguish different components or tissue types by specified or predetermined threshold values. Without the application of the method the differences that may be observed with different target objects or patients and/or with different X-ray devices or calibrations may lead to inconsistencies or errors in the application of such HU threshold value methods or algorithms. It is only due to the method that consistently automatic processing of image data sets is reliably made possible, therefore.

The terms "pixel" and "pixel value" may refer, for example, to 2D pixels or to 3D voxels.

In an embodiment, for determining the reference image, a respective largest cohesive region for the corresponding component, or the largest cohesive component, is individually determined for each of the binary masks and then the respective determined largest cohesive regions of all of the binary masks are compared with each other. A respective number of the pixels or values of the respective largest cohesive regions of all binary masks may be determined and compared with each other. One cohesive region is therefore larger than another cohesive region if it includes a greater number of pixels or voxels. As a result, one of the binary masks is determined therefore, which, of all of the binary masks, includes the largest cohesive region of a particular one of the two binary values. The reference image is then that one of the single images associated with the determined binary mask, that one of the single images from which the respective determined binary mask has been generated. Since the binary masks are much less complex compared to the underlying single images, the method may be applied quickly and with low computing effort which supports a real-time application of the method.

In an embodiment, two different CT numbers are specified as the threshold values for generating the binary masks, by which numbers, air is differentiated from soft tissue and soft tissue is differentiated from bone. For generating the binary masks from the single images, the pixels thereof, for pixel values lying between the two specified CT numbers, a first value is allocated to the binary mask, and for pixel values, that lie below the smaller or above the larger of the two CT numbers, a second value is allocated to the binary mask. The two specified CT numbers, that is to say HU or X-ray damping values, distinguish or differentiate three different components of the categories of components of the target object. However, two of the components or categories are allocated the same value in the binary mask. The soft tissue may be differentiated or isolated particularly accurately and reliably hereby. By definition air has a CT number of −1,000 HU and water a CT number of 0 HU. Fatty tissue may include, for example, a CT number of −100 HU, while bones, depending on density, may include, for example, a CT number between 500 HU and 1,500 HU. Preferably, the lower of the two specified CT numbers may therefore lie, for example, between −500 HU and −150 HU and the larger of the two specified CT numbers between 50 HU and 400 HU. The soft tissue may be reliably distinguished hereby, in other words differentiated, from air and bone regions despite the described potential differences between different target objects and/or X-ray devices.

In an embodiment, a low-pass filter, e.g. a 3D low-pass filter, is applied to the acquired image data set before generation of the binary masks. A limit frequency or time constant of the low-pass filter may be specified as required or depending on the application or may be automatically or dynamically determined. A noise reduction in the image data set may be achieved by applying, the low-pass filter. Ultimately, an improved image quality of the adapted image data set may be achieved thereby. In addition, a more reliable differentiation of the various components of the target object by way of the binary masks may optionally be achieved.

In an embodiment, after generation of the binary masks, an erosion operation is applied to the binary masks before the reference image is determined. Due to the erosion operation, values of isolated pixels in each of the binary masks are set at the other one of the two binary values or mask values respectively. If, for example, one of the binary masks includes a cohesive region comprising pixels including the binary mask value 0 and located within the cohesive region is a single, e.g. isolated, pixel including the binary mask value 1, then, due to the erosion operation, the binary mask value of the single isolated pixel is set from 1 to 0. This takes account of the knowledge that isolated pixels represent either an image artifact or are irrelevant to the evaluation or diagnosis of the target object.

An isolated pixel is a pixel that within the respective binary mask is surrounded on all sides by pixels that include the other one of the two binary values respectively. Similarly, a number threshold value may be specified for a number or quantity of pixels, whose values are set at the other value respectively if the pixels are surrounded on all sides by pixels including the other binary value respectively. For example, two or more adjacent pixels including the same binary value may be regarded and treated as isolated pixels if the two or more adjacent pixels are surrounded by pixels of the other binary value respectively.

Due to the erosion operation, a distribution of the binary values within the respective binary masks is therefore smoothed. As a result, computing effort and time expenditure when determining the largest cohesive region(s) may be reduced and the method accelerated, without a validity of the resulting adapted image data set being limited hereby. In a specific application, due to the erosion operation, for example brain tissue may be differentiated from the scalp and/or neck tissue.

In an embodiment for determining the offset, the specified target value is subtracted from the determined mean value. For adapting the image data set, the determined offset is subtracted from all pixel values of the image data set. The offset may be signed, so in the case of a negative offset, the subtraction effectively corresponds to an addition of an amount of the determined offset to the respective pixel values. Adaptation of the image data set may be carried out easily, quickly and in an understandable way. Because the offset is applied to all pixel values of the image data set in the same way, a ratio, for example a contrast ratio, is retained or maintained between different pixels or components of the original image data set even in the adapted image data set. Therefore, no image information is lost due to the adaptation of the image data set.

In an embodiment the target object is automatically recognized by an object recognition algorithm. As a function of the recognized target object or type, the target value for determining the offset is then automatically selected from a plurality of target values specified for different target objects or different types of target objects. Recognition of the target object may lead to that by the object recognition algorithm, e.g. by automatic processing of the image data set, the kind or the type or the like of the target object is determined, for example in other words which body part or which organ of the image data set is imaged. As a result, the suitable target value may be reliably automatically determined or selected. The object recognition or image processing algorithm may be carried out or implemented for example by a neural network. The method may be automated further by the automatic recognition of the target object, whereby an error rate, for example due to avoidance of operating or input errors, may be reduced.

Recognition of the target object may similarly also include an individual identification. For example, the individual differences, already discussed, for different target objects, e.g. patients may be taken into account. The respective target object, e.g. respective patient, may be examined or imaged several times. The threshold value for generating the binary masks may likewise be determined or selected as a function of the automatically recognized target object or an identity. As a result, the different components of the target object in the single images may be reliably distinguished or differentiated from each other since, for example, as described, individual properties of the respective target object may be taken into account.

In an embodiment, using the adapted image data set and at least one likewise correspondingly adapted further image data set, a differentiation threshold value is automatically determined that provides a clear distinguishing or differentiation of two components of the target objects. The adapted image data set and the at least one further image data set image map similar target objects. A plurality of image data sets of different but similar target objects are evaluated to determine the differential threshold value. The differential threshold value may then be consistently and reliably used by further automatic image processing or image evaluation algorithms or methods. The differentiation threshold value may then be reliably used also for other data sets of corresponding target objects to distinguish respective components therein from each other.

Target objects are similar if, for example, the target objects map the same body part or the same organ or the same tissue types of the various target objects or patients.

In an embodiment, a head of a patient is at least partially mapped by the image data set as the target object. The adapted image data set and the differentiation threshold value are supplied as input data to an image processing algorithm. The image processing algorithm automatically determines on the basis of the differentiation threshold value and using the adapted image data set automatically an infarct core volume present in the head. The method may be applied with DynaCT scans. For automatic determination of the infarct core volume the image processing algorithm is reliant on reliable, absolute HU values in the underlying adapted image data set. The absolute HU values are reliably and consistently adjusted by the method for different target objects and at different calibrations of the X-ray device. By way of the method, the target object may be mapped, e.g. acquire the image data set, and also to evaluate the image data set automatically. Consequently, the evaluation may be carried out quickly, consistently and with reduced error rates.

An embodiment provides a computer program that encodes or represents the method steps of at least one embodiment of the method for automatically adapting an image data set obtained by an X-ray device. The computer program for carrying out the method steps or the method by the X-ray device may be loaded in a data memory of a control device of the X-ray device. The computer program may include programming to carry out the method when the computer program is carried out by the control device.

An embodiment provides an electronically readable, data memory or data carrier for a control device of an X-ray device. A program code is stored in the data memory, that includes at least one computer program. In addition, further control instructions for the control device and/or the X-ray device may be stored or encoded in the data memory, e.g. as part of the program code. The program code stored on the data memory is configured to bring about at least one embodiment of the method when the data memory is used in the control device of the X-ray device and when the program code is executed by the control device, for example, by a microprocessor and/or microcontroller of the control device.

An embodiment provides an X-ray device, for example, a computed tomography device (CT device), including an acquisition facility for acquiring a plurality of single images of a target object, that map different slices or planes of the target object and together form an image data set. The X-ray device includes a data processing facility for automatically processing the acquired image data set. The X-ray device, e.g. data processing facility, is configured for automatically carrying out at least one embodiment of the method for automatically adapting the image data set obtained or acquired by the X-ray device. The X-ray device may include some or all of the facilities, components and/or properties described in connection with the other aspects, including for example, the acquisition facility for automatic recognition of the target object.

The data processing facility of the X-ray device may include a data memory with a program code, that encodes or represents the method steps of the corresponding method. The program code may be the computer program or include it. Furthermore, the data processing facility includes a processor connected to the data memory, for example a microprocessor, that is arranged and adapted to execute program code stored on the data memory and thereby carry out the corresponding method. The X-ray device may be configured to carry out or record an angiography.

DETAILED DESCRIPTION

Figure 1:
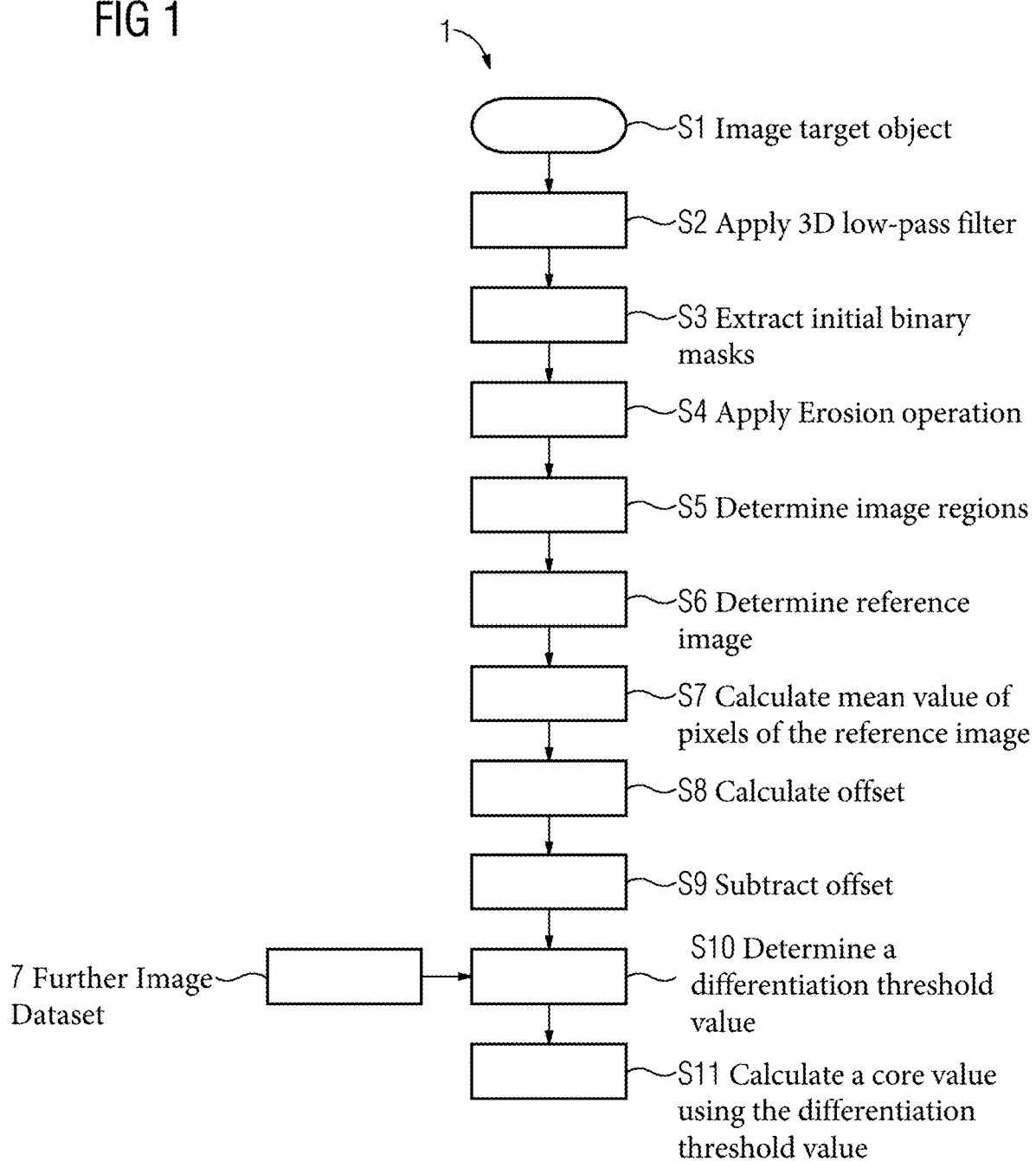
FIG. 1 depicts a schematic flowchart of a method for automatically adapting an image data set obtained by an X-ray device according to an embodiment.

FIG. 1 depicts a schematic flowchart 1 of a method for automatically adapting an image data set obtained by an X-ray device, that maps a target object.

Figure 2:
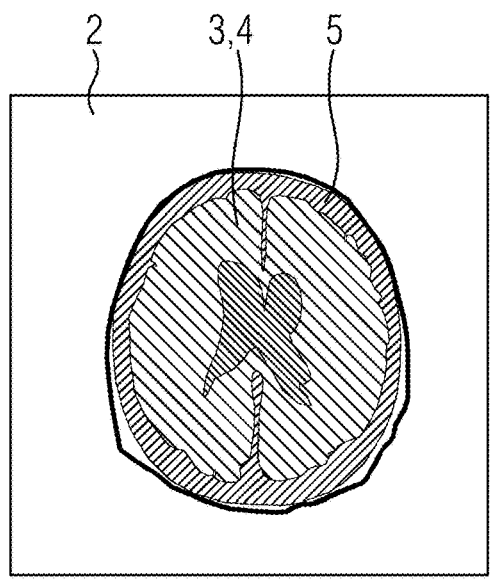
FIG. 2 depicts a single image of the image data set before the adaptation thereof according to an embodiment.

The method includes a method step S1. The corresponding X-ray device may be activated and the target object imaged for acquisition of the image data set. The image data set includes a plurality of single images, that correspond to different slices of the target object. FIG. 2 depicts a single image 2 of the image data set, with a head 3 of a patient being mapped as the target object. At least two different tissue types or components are imaged including a brain as the first component 4 and a skull or bone tissue as the second component 5. The single image 2 is part of the original, in other words un-adapted, image data set.

A high-quality display, for example of both soft tissue as well as a dynamic perfusion in the brain tissue, is possible by way of an available X-ray devices, for example an angiograph system. However, absolute intensity or HU values of corresponding scans or images are less reliable than, for example, X-ray images obtained by a Helix CT method. Therefore, for example absolute HU values may differ significantly from each other, for instance for a cerebrospinal fluid (CSF) or a white brain substance, in corresponding images of different patients. This is a problem against the background that currently available software, for example for automated calculation of infarct volumes on perfusion scans, uses methods, that are based on HU threshold values, using which, for example, the CSF is detected or distinguished from other tissue types. It is only with reliable detection that the image region that maps the CSF may then actually consistently be rejected or ignored on calculation of the infarct volume.

Figure 3:
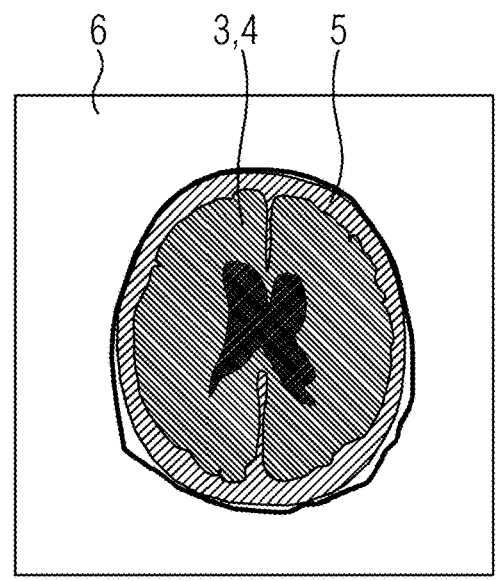
FIG. 3 depicts the single image of FIG. 3 after the adaptation of the image data set according to an embodiment.

One result of the adaptation of the image data set by the method explained in more detail below is shown in FIG. 3 in the form of an adapted single image 6. The adapted single image 6 results from the application of the method to the single image 2 shown in FIG. 2. The adapted single image 6 shows the head 3 with the two components 4, 5, albeit with, compared to the single image 2, adapted or normalized HU values, in other words brightness or intensity values.

To obtain the adapted single image 6 from the un-adapted single image 2, a 3D low-pass filter for initial noise reduction is applied to the acquired un-adapted image data set in a method step S2.

In a method step S3 respective initial binary masks are extracted or generated from the single images of the image data set using specified threshold values. The masks differentiate soft tissue from air and bone in the single images, for example, the first component 4 from the second component 5. Each pixel of the single images is allocated one of two binary values respectively, from which the binary masks are formed, as a function of whether the HU value of the respective pixel lies for example between the specified threshold values or outside of the specified threshold values or outside of an interval defined by the specified threshold values. A binary mask determined from a particular single image includes the same number and arrangement of pixels as the single image underlying the respective binary mask. Since the respective binary mask is generated alternately or pixel accurately from the respective underlying single image, there is a clear association between pixels of the single image and the pixels of the associated binary mask generated from the single image.

Since the image data set may be a reconstructed volume, pixels may also include voxels of the single images or of the image data set.

An erosion operation is applied to the binary masks in a method step S4. As a result, pixels isolated in the binary masks are adapted to respective surrounding pixels, so ultimately only larger cohesive regions remain or are left in the binary masks. Which pixels or pixel regions are treated as isolated, and are accordingly changed in value, may be determined by a specified number threshold value, that indicates the corresponding maximum number of cohesive pixels, that are still considered isolated. By the application of the erosion operation, for example pixels or image regions of such pixels or image regions that map or represent the brain tissue, e.g. in a cerebellum, may be separated or differentiated, that represent or map a scalp or neck tissue.

A respective largest cohesive image and pixel region is determined for each of the binary masks in a method step S5. Due to the underlying threshold value and the erosion operation, the pixels that include the same pixel or binary value in the respective binary mask correspond to the same component of the patient. For example, pixels or regions of one of the binary masks, that include the pixel or binary value 1, correspond to the brain tissue, in other words the first component 4, while pixels or regions of the binary mask, that include the pixel or binary value 0, correspond to other tissue types, for instance the second component 5. In method step S5 the corresponding largest cohesive pixel or image regions are determined for all binary masks for a specified binary value or for a specified component—here for the first component 4—which regions in the underlying single image respectively therefore correspond to the largest cohesive regions of the respective component or tissue types.

In a method step S6, using the binary masks or using the largest cohesive regions determined for them, that one of the single images is determined in which, of all the single images, the largest cohesive region of the specified component is contained or displayed. One of the mapped slices including the most pixels or voxels pertaining to the corresponding component, here for example to the brain tissue, is determined. The associated single image is then determined or defined as a reference image.

Figure 4:
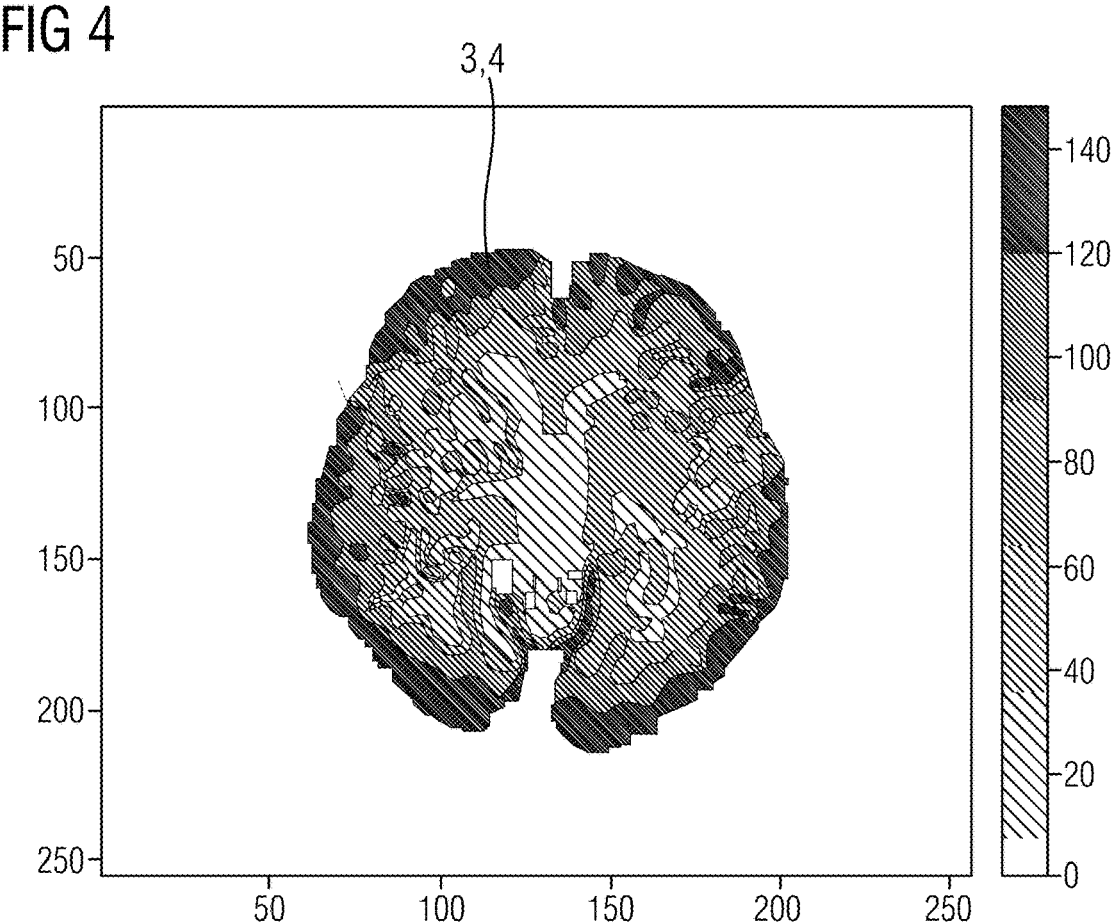
FIG. 4 depicts pixels of a single image of the image data set associated with a first tissue component according to an embodiment.

In a method step S7 the pixels of the reference image, corresponding to the determined largest cohesive region of the binary mask associated with the reference image, and their mean value, e.g. the average HU value, are calculated. FIG. 4 depicts the pixels selected for determining the mean value. FIG. 4 depicts only the first component 4, but not the second component 5. The mean value of the pixel or HU values of the pixels pertaining to the first component 4 is here approximately 83 HU.

In a method step S8 an offset is calculated using the mean value calculated in method step S7 and a target value specified here for the first component 4. The specified target value is subtracted from the calculated mean value. The offset is determined and calculated such that, after a mathematical subtraction of the offset, a resulting new mean value of the pixels or pixel values used in method step S6, depicted in FIG. 4, corresponds to the specified target value—of here, for example, 30 HU.

In a method step S9, for adapting the image data set, the determined offset is subtracted from all pixel or voxel values of the entire un-adapted image data set, e.g. all single images.

The adapted image data set is supplied together with at least one correspondingly adapted further image data set 7 to a data processing facility.

Figure 5:
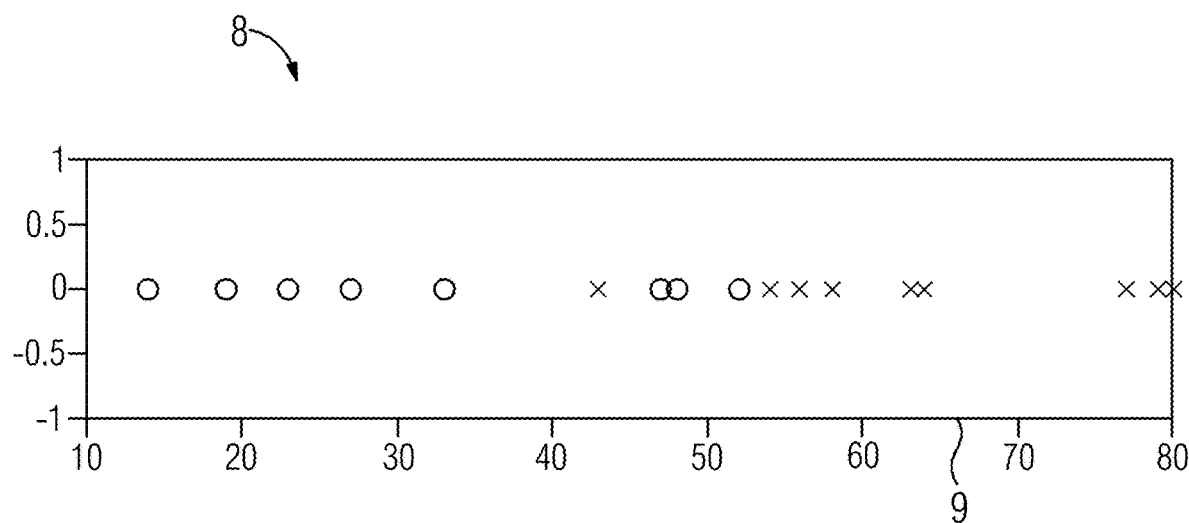
FIG. 5 depicts a distribution of HU values, determined from un-adapted image data sets, for two different tissue types of a plurality of different patients according to an embodiment.

FIG. 5 depicts a distribution 8 of HU values for two different tissue types of a plurality of different patients determined from corresponding un-adapted image data sets. HU values are plotted on an X axis 9. For the example, the CSF was used as the first tissue type and the brain tissue as the second tissue type. Values or data points pertaining to the CSF are identified by "o" and values or data points pertaining to the brain tissue by "x". The individual values or data points correspond to HU means in, similar, tissue types or regions of interest (ROI) of the different patients. A value pair from a value for the CSF and a value for the brain tissue is plotted for each patient. Owing to the individual differences in the patients and/or the acquisition conditions of the underlying image data sets, the data points pertaining to the different tissue types, in other words components, cannot be differentiated from each other by a single absolute threshold value. There is therefore no single HU value, by which the data points for the two components are distributed into two uniform groups, for which it is therefore true that all data points pertaining to the one component lie above and all data points pertaining to the other component lie below the HU value.

Figure 6:
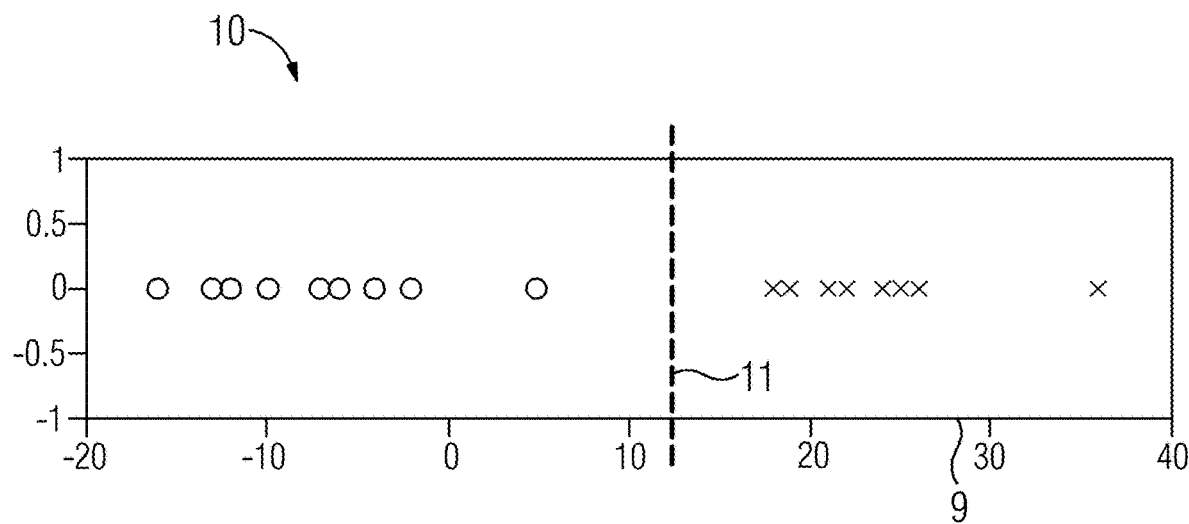
FIG. 6 depicts a distribution of HU values, determined from adapted image data sets, for two different tissue types of different patients according to an embodiment.

In a method step S10 the data processing facility determines from the supplied image data sets a differentiation threshold value 11 (see FIG. 6), by which a clear differentiation of the data points pertaining to the two different tissue types is possible on the basis the adapted image data sets. FIG. 6 shows in this regard an adapted distribution 10 of the HU values from FIG. 5. The adapted distribution 10 results by application of the described method to the image data sets underlying the distribution 8, in other words their adaptation by subtraction of the respective, individually determined offset.

By adapting the image data sets according to the described method, it is now possible to define the differentiation threshold value 11 as an absoluter HU value in the adapted distribution 10, by which the data points pertaining to the first tissue type may be clearly distinguished or separated from the data points pertaining to the tissue type. The adapted distribution 10 shows the distribution 8 of the HU values from FIG. 5 after the normalization of the HU values of the underlying image data sets. In the example, the differentiation threshold value 11 is chosen such that it lies centrally between the largest value pertaining to the first tissue type and the smallest value pertaining to the second tissue type and in the present example is 12 HU.

In a method step S11 an infarct core volume given, e.g. mapped, in the adapted image data set is automatically calculated by the data processing facility using the differentiation threshold value 11. Pixels whose adapted or normalized HU values are smaller than the differentiation threshold value 11 are ignored.

Overall, the described examples show how a novel and fully automatic method may be implemented in order to reliably correct individual differences in X-ray image data sets or X-ray scans. Reliable, in other words consistent and comparable, absolute HU values are determined in the process, providing an application of algorithms, that use HU threshold values in the soft tissue region, for example for DynaCT, e.g. for software for automatic calculation of infarct core volumes.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically adapting an image data set obtained by an X-ray device, that maps a target object, the method comprising:
    acquiring the image data set comprising a plurality of single images that map different layers of the target object;
    generating a respective binary mask for each of the plurality of single images using at least one specified threshold value, wherein the respective binary masks differentiate different components of the target object in the plurality of single images from each other;
    determining, using all of the binary masks, one of the plurality of single images that contains a largest cohesive region of one of the components as a reference image;
    determining a mean value of all pixel values of the reference image pertaining to the largest cohesive region;
    determining an offset from the determined mean value and a specified target value such that by applying the offset to the pixel values used for determining the mean value, the pixel values are adapted such that a mean value of the pixel values adapted by the offset corresponds to the specified target value; and
    adapting the image data set by applying the determined offset to all pixel values of the image data set.

2. The method of claim 1, wherein determining the reference image comprises:
    determining a respective largest cohesive region for each of the binary masks; and
    comparing the respective largest cohesive regions of all of the binary masks with each other.

3. The method of claim 1, wherein two different CT numbers are specified as threshold values for generating the binary masks, by which air is differentiated from soft tissue and soft tissue is differentiated from bone, wherein for generating the binary masks from the plurality of single images, for pixel values lying between the two different CT numbers, a first value is allocated to the binary masks, and for pixel values, that lie below the smaller or above the larger of the two different CT numbers, a second value is allocated to the binary masks.

4. The method of claim 1, wherein a low-pass filter is applied to the image data set before generation of the binary masks.

5. The method of claim 1, wherein after generation of the binary masks, an erosion operation is firstly applied to the binary masks before the reference image is determined.

6. The method of claim 1, wherein for determining the offset, the specified target value is subtracted from the determined mean value and for adapting the image data set, the determined offset is subtracted from all pixel values of the image data set.

7. The method of claim 1, wherein the target object is automatically recognized by an object recognition algorithm, and as a function of the recognized target object, the specified target value for determining the offset is automatically selected from a plurality of target values specified for different target objects.

8. The method of claim 1, wherein by using the adapted image data set and at least one likewise correspondingly adapted further image data set that map similar target objects, a differentiation threshold value is automatically determined that provides a clear differentiation of two components of the similar target objects.

9. The method of claim 8, further comprising:
mapping a head of a patient as the target object using the image data set;
providing the adapted image data set and the differentiation threshold value as input data to an image processing algorithm; and
determining an infarct core volume present in the head using the image processing algorithm.

10. A non-transitory computer implemented storage medium that stores machine-readable instructions executable by at least one processor for automatically adapting an image data set obtained by an X-ray device, the machine-readable instructions comprising:
acquiring the image data set comprising a plurality of single images that map different layers of a target object;
generating a respective binary mask for each of the plurality of single images using at least one specified threshold value, wherein the respective binary masks differentiate different components of the target object in the plurality of single images from each other;
determining, using all of the binary masks, one of the plurality of single images that contains a largest cohesive region of one of the components as a reference image;
determining a mean value of all pixel values of the reference image pertaining to the largest cohesive region;
determining an offset from the determined mean value and a specified target value such that by applying the offset to the pixel values used for determining the mean value, the pixel values are adapted such that a mean value of the pixel values adapted by the offset corresponds to the specified target value; and
adapting the image data set by applying the determined offset to all pixel values of the image data set.

11. The non-transitory computer implemented storage medium of claim 10, wherein determining the reference image comprises:
determining a respective largest cohesive region for each of the binary masks; and
comparing the respective largest cohesive regions of all of the binary masks with each other.

12. The non-transitory computer implemented storage medium of claim 10, wherein two different CT numbers are specified as threshold values for generating the binary masks, by which air is differentiated from soft tissue and soft tissue is differentiated from bone, wherein for generating the binary masks from the plurality of single images, for pixel values lying between the two different CT numbers, a first value is allocated to the binary masks, and for pixel values, that lie below the smaller or above the larger of the two different CT numbers, a second value is allocated to the binary masks.

13. The non-transitory computer implemented storage medium of claim 10, wherein a low-pass filter is applied to the image data set before generation of the binary masks.

14. The non-transitory computer implemented storage medium of claim 10, wherein after generation of the binary masks, an erosion operation is firstly applied to the binary masks before the reference image is determined.

15. The non-transitory computer implemented storage medium of claim 10, wherein for determining the offset, the specified target value is subtracted from the determined mean value and for adapting the image data set, the determined offset is subtracted from all pixel values of the image data set.

16. The non-transitory computer implemented storage medium of claim 10, wherein the target object is automatically recognized by an object recognition algorithm, and as a function of the recognized target object, the specified target value for determining the offset is automatically selected from a plurality of target values specified for different target objects.

17. The non-transitory computer implemented storage medium of claim 10, wherein by using the adapted image data set and at least one likewise correspondingly adapted further image data set that map similar target objects, a differentiation threshold value is automatically determined that provides a clear differentiation of two components of the similar target objects.

18. An X-ray device comprising:
an acquisition facility configured to acquire a plurality of single images of a target object that map different slices of the target object and together form an image data set; and
a data processor configured to:
generate a respective binary mask for each of the plurality of single images using at least one specified threshold value, wherein the respective binary masks differentiate different components of the target object in the plurality of single images from each other;
determine, using all of the binary masks, one of the plurality of single images that contains a largest cohesive region of one of the components as a reference image;
determine a mean value of all pixel values of the reference image pertaining to the largest cohesive region;
determine an offset from the determined mean value and a specified target value such that by applying the offset to the pixel values used for determining the mean value, the pixel values are adapted such that a mean value of the pixel values adapted by the offset corresponds to the specified target value; and apply the determined offset to all pixel values of the image data set.

\* \* \* \* \*